(12) United States Patent
Dorn

(10) Patent No.: US 9,072,623 B2
(45) Date of Patent: *Jul. 7, 2015

(54) LOADING AND DELIVERY OF SELF-EXPANDING STENTS

(71) Applicant: C. R. Bard, Inc., Murray Hill, NJ (US)

(72) Inventor: Jurgen Dorn, Neulussheim (DE)

(73) Assignee: C. R. BARD, INC., Murray Hills, NJ (US)

( * ) Notice: Subject to any disclaimer, the term of this patent is extended or adjusted under 35 U.S.C. 154(b) by 168 days.

This patent is subject to a terminal disclaimer.

(21) Appl. No.: 13/648,781

(22) Filed: Oct. 10, 2012

(65) Prior Publication Data

US 2013/0079863 A1 Mar. 28, 2013

Related U.S. Application Data

(62) Division of application No. 10/552,886, filed as application No. PCT/EP2004/004486 on Apr. 28, 2004, now Pat. No. 8,287,582.

(30) Foreign Application Priority Data

Apr. 28, 2003 (GB) .................................. 0309616.1

(51) Int. Cl.
*A61F 2/06* (2013.01)
*A61F 2/95* (2013.01)
*A61F 2/966* (2013.01)

(52) U.S. Cl.
CPC . *A61F 2/95* (2013.01); *A61F 2/966* (2013.01); *A61F 2002/9522* (2013.01)

(58) Field of Classification Search
CPC ........................ A61F 2/95; A61F 2002/9665
USPC ................................ 623/1.11; 606/194, 198
See application file for complete search history.

(56) References Cited

U.S. PATENT DOCUMENTS

| 4,576,534 A | 3/1986 | Barth et al. |
| 4,580,568 A | 4/1986 | Gianturco |
| 4,719,853 A | 1/1988 | Bowers |

(Continued)

FOREIGN PATENT DOCUMENTS

| CA | 2537366 A1 | 4/2005 |
| DE | 10016920 A1 | 10/2001 |

(Continued)

OTHER PUBLICATIONS

CA 2,523,557 filed Apr. 28, 2004 Offical Action dated Aug. 20, 2010.

(Continued)

*Primary Examiner* — Tuan V Nguyen
*Assistant Examiner* — Chima Igboko
(74) *Attorney, Agent, or Firm* — Buchalter Nemer

(57) ABSTRACT

A method of deploying a stent includes providing a delivery system with the stent loaded in a reduced diameter configuration between an inner catheter and an outer sheath, the stent including a covering positioned on a luminal wall surface thereof, the inner catheter including a radially outwardly extending protrusion that extends into the covering but does not intersect a plane along the stent luminal wall surface, advancing the delivery system to a stenting site, and withdrawing the outer sheath to deploy the stent at the stenting site.

20 Claims, 2 Drawing Sheets

(56) References Cited

U.S. PATENT DOCUMENTS

| | | | |
|---|---|---|---|
| 4,762,128 A * | 8/1988 | Rosenbluth | 606/192 |
| 4,768,507 A | 9/1988 | Fischell et al. | |
| 4,950,227 A | 8/1990 | Savin et al. | |
| 5,026,377 A | 6/1991 | Burton et al. | |
| 5,037,427 A | 8/1991 | Harada et al. | |
| 5,201,757 A | 4/1993 | Heyn et al. | |
| 5,201,901 A | 4/1993 | Harada et al. | |
| 5,458,605 A | 10/1995 | Klemm | |
| 5,480,423 A | 1/1996 | Ravenscroft et al. | |
| 5,484,444 A | 1/1996 | Braunschweiler et al. | |
| 5,520,645 A | 5/1996 | Imran et al. | |
| 5,554,181 A | 9/1996 | Das | |
| 5,562,641 A | 10/1996 | Flomenblit et al. | |
| 5,562,726 A | 10/1996 | Chuter | |
| 5,569,295 A | 10/1996 | Lam | |
| 5,569,296 A | 10/1996 | Marin et al. | |
| 5,591,222 A | 1/1997 | Susawa et al. | |
| 5,609,627 A | 3/1997 | Goicoechea et al. | |
| 5,619,878 A | 4/1997 | Grosjean et al. | |
| 5,645,559 A | 7/1997 | Hachtman et al. | |
| 5,683,451 A | 11/1997 | Lenker et al. | |
| 5,697,948 A | 12/1997 | Marin et al. | |
| 5,702,418 A | 12/1997 | Ravenscroft | |
| 5,709,703 A | 1/1998 | Lukic et al. | |
| 5,749,880 A | 5/1998 | Banas et al. | |
| 5,749,921 A | 5/1998 | Lenker et al. | |
| 5,755,777 A | 5/1998 | Chuter | |
| 5,776,141 A | 7/1998 | Klein et al. | |
| 5,807,327 A | 9/1998 | Green et al. | |
| 5,824,040 A | 10/1998 | Cox et al. | |
| 5,824,041 A | 10/1998 | Lenker et al. | |
| 5,843,167 A | 12/1998 | Dwyer et al. | |
| 5,876,448 A | 3/1999 | Thompson et al. | |
| 5,902,334 A | 5/1999 | Dwyer et al. | |
| 5,913,871 A | 6/1999 | Werneth et al. | |
| 5,920,975 A | 7/1999 | Morales | |
| 5,928,258 A | 7/1999 | Khan et al. | |
| 5,968,068 A | 10/1999 | Dehdashtian et al. | |
| 5,976,155 A * | 11/1999 | Foreman et al. | 623/1.11 |
| 5,980,532 A | 11/1999 | Wang | |
| 5,980,548 A | 11/1999 | Evans et al. | |
| 5,989,280 A | 11/1999 | Euteneuer et al. | |
| 6,033,388 A | 3/2000 | Nordstrom et al. | |
| 6,048,350 A | 4/2000 | Vrba | |
| 6,056,906 A | 5/2000 | Werneth et al. | |
| 6,063,092 A | 5/2000 | Shin | |
| 6,077,295 A | 6/2000 | Limon et al. | |
| 6,110,142 A | 8/2000 | Pinchuk et al. | |
| 6,110,180 A | 8/2000 | Foreman et al. | |
| 6,110,191 A | 8/2000 | Dehdashtian et al. | |
| 6,113,628 A | 9/2000 | Borghi et al. | |
| 6,132,458 A | 10/2000 | Staehle et al. | |
| 6,143,014 A | 11/2000 | Dehdashtian et al. | |
| 6,203,568 B1 | 3/2001 | Lombardi et al. | |
| 6,210,429 B1 | 4/2001 | Vardi et al. | |
| 6,214,039 B1 | 4/2001 | Banas et al. | |
| 6,245,099 B1 | 6/2001 | Edwin et al. | |
| 6,258,099 B1 * | 7/2001 | Mareiro et al. | 606/108 |
| 6,302,893 B1 | 10/2001 | Limon et al. | |
| 6,302,906 B1 | 10/2001 | Goicoechea et al. | |
| 6,306,162 B1 * | 10/2001 | Patel | 623/1.11 |
| 6,319,275 B1 | 11/2001 | Lashinski et al. | |
| 6,322,586 B1 | 11/2001 | Monroe et al. | |
| 6,352,531 B1 | 3/2002 | O'Connor et al. | |
| 6,451,047 B2 | 9/2002 | McCrea et al. | |
| 6,471,718 B1 | 10/2002 | Staehle et al. | |
| 6,500,202 B1 | 12/2002 | Shaolian et al. | |
| 6,576,006 B2 | 6/2003 | Limon et al. | |
| 6,607,551 B1 * | 8/2003 | Sullivan et al. | 623/1.11 |
| 6,613,075 B1 | 9/2003 | Healy et al. | |
| 6,620,172 B1 | 9/2003 | Dretler et al. | |
| 6,758,858 B2 | 7/2004 | McCrea et al. | |
| 6,776,791 B1 | 8/2004 | Stallings et al. | |
| 6,796,998 B2 | 9/2004 | Schaldach et al. | |
| 6,858,034 B1 | 2/2005 | Hijlkema et al. | |
| 6,945,989 B1 | 9/2005 | Betelia et al. | |
| 7,011,675 B2 * | 3/2006 | Hemerick et al. | 623/1.12 |
| 7,717,949 B2 | 5/2010 | Dorn | |
| 7,867,267 B2 | 1/2011 | Sullivan et al. | |
| 7,935,140 B2 * | 5/2011 | Griffin | 623/1.11 |
| 8,287,582 B2 | 10/2012 | Dorn | |
| 2001/0032009 A1 | 10/2001 | Layne et al. | |
| 2001/0039446 A1 | 11/2001 | Edwin et al. | |
| 2001/0049549 A1 | 12/2001 | Boylan et al. | |
| 2002/0010489 A1 * | 1/2002 | Grayzel et al. | 606/194 |
| 2002/0029076 A1 | 3/2002 | Yee | |
| 2002/0038143 A1 | 3/2002 | McCrea et al. | |
| 2002/0058993 A1 | 5/2002 | Landau et al. | |
| 2002/0138966 A1 | 10/2002 | Motsenbocker | |
| 2002/0147490 A1 | 10/2002 | Pletzer et al. | |
| 2002/0156516 A1 | 10/2002 | Vardi et al. | |
| 2002/0193863 A1 | 12/2002 | Rourke et al. | |
| 2003/0032999 A1 | 2/2003 | Huang | |
| 2003/0153969 A1 | 8/2003 | Dehdashtian et al. | |
| 2004/0093061 A1 * | 5/2004 | Acosta et al. | 623/1.11 |
| 2004/0106977 A1 * | 6/2004 | Sullivan et al. | 623/1.12 |
| 2004/0143272 A1 | 7/2004 | Cully et al. | |
| 2004/0204749 A1 * | 10/2004 | Gunderson | 623/1.12 |
| 2006/0184225 A1 | 8/2006 | Pryor | |
| 2006/0184226 A1 | 8/2006 | Austin | |
| 2006/0216404 A1 | 9/2006 | Seyler et al. | |
| 2006/0259123 A1 | 11/2006 | Dorn | |
| 2006/0271149 A1 * | 11/2006 | Berez et al. | 623/1.11 |
| 2007/0024072 A1 | 2/2007 | Leon | |
| 2007/0083256 A1 | 4/2007 | Dorn | |
| 2007/0156251 A1 | 7/2007 | Karmon | |
| 2010/0070016 A1 | 3/2010 | Dorn et al. | |

FOREIGN PATENT DOCUMENTS

| | | |
|---|---|---|
| DE | 10212707 A1 | 10/2003 |
| DE | 20306823 U1 | 11/2003 |
| EP | 0596145 A1 | 5/1994 |
| EP | 0775470 A1 | 5/1997 |
| EP | 0788332 | 8/1997 |
| EP | 0826346 | 3/1998 |
| EP | 0834293 A1 | 4/1998 |
| EP | 0836447 A2 | 4/1998 |
| EP | 0873731 | 10/1998 |
| EP | 1382367 A1 | 1/2004 |
| EP | 1466570 A1 | 10/2004 |
| FR | 2742042 A1 | 6/1997 |
| FR | 2760351 A1 | 9/1998 |
| JP | 08-141090 A | 6/1996 |
| JP | 11-512318 T | 10/1999 |
| JP | 2001-501115 T | 1/2001 |
| JP | 2002-501404 T | 1/2002 |
| JP | 2003-500103 T | 1/2003 |
| JP | 2003-500104 T | 1/2003 |
| JP | 2005-038367 A | 2/2005 |
| JP | 2007-024072 A | 2/2007 |
| WO | 9533422 A1 | 12/1995 |
| WO | 9628115 A1 | 9/1996 |
| WO | 9639998 A2 | 12/1996 |
| WO | 9709932 A1 | 3/1997 |
| WO | 9814233 A1 | 4/1998 |
| WO | 9831305 A1 | 7/1998 |
| WO | 9853761 A1 | 12/1998 |
| WO | 9955255 | 11/1999 |
| WO | 0071057 A1 | 11/2000 |
| WO | 0071058 A1 | 11/2000 |
| WO | 0105331 | 1/2001 |
| WO | 0121103 A2 | 3/2001 |
| WO | 0134061 A1 | 5/2001 |
| WO | 0215820 A2 | 2/2002 |
| WO | 03003944 A2 | 1/2003 |
| WO | 03024362 A1 | 3/2003 |
| WO | 03049641 A1 | 6/2003 |
| WO | 2004062458 A2 | 7/2004 |
| WO | 2004096091 A1 | 11/2004 |

(56) References Cited

FOREIGN PATENT DOCUMENTS

| WO | 2006026377 A1 | 3/2006 |
| WO | 2007149464 A2 | 12/2007 |

OTHER PUBLICATIONS

JP 2006-505303 filed Feb. 16, 2006 Office Action dated Mar. 23, 2010.
JP 2006-527350 Examination Report (translated) dated Aug. 6, 2009.
PCT/EP2004/004486 filed Apr. 28, 2004 International Preliminary Report on Patentability dated Oct. 28, 2005.
PCT/EP2004/004486 filed Apr. 28, 2004 Search Report dated Sep. 27, 2004.
PCT/EP2004/004486 filed Apr. 28, 2004 Written Opinion dated Sep. 27, 2004.
PCT/EP2009/061918 filed Sep. 5, 2009 Search Report dated Nov. 25, 2009.
PCT/EP200/061918 filed Sep. 15, 2009 Written Opinion dated Nov. 25, 2009.
PCT/US2000/014038 filed May 19, 2000 International Preliminary Examination Report dated Jul. 31, 2001.
PCT/US2000/014038 filed May 19, 2000 Search Report dated Sep. 13, 2000.
U.S. Appl. No. 10/552,886, filed Nov. 18, 2005 Non-Final Office Action dated Sep. 28, 2007.
U.S. Appl. No. 10/552,886, filed Nov. 18, 2005 Final Office Action dated Oct. 29, 2008.
U.S. Appl. No. 10/552,886, filed Nov. 18, 2005 Non-Final Office Action dated Apr. 2, 2008.
U.S. Appl. No. 10/552,886, filed Nov. 18, 2005 Non-Final Office Action dated Sep. 8, 2007.
U.S. Appl. No. 10/552,886, filed Nov. 18, 2005 Decision on Appeal dated Jan. 11, 2012.
U.S. Appl. No. 10/552,886, filed Nov. 18, 2005 Notice of Allowance dated May 18, 2012.
U.S. Appl. No. 10/572,191, filed Apr. 11, 2006 Advisory Action dated Jan. 2, 2009.
U.S. Appl. No. 10/572,191, filed Apr. 11, 2006 Final Office Action dated Jun. 8, 2009.
U.S. Appl. No. 10/572,191, filed Apr. 11, 2006 Final Office Action dated Oct. 10, 2008.
U.S. Appl. No. 10/572,191, filed Apr. 11, 2006 Final Office Action dated Oct. 5, 2009.
U.S. Appl. No. 10/572,191, filed Apr. 11, 2006 Non-Final Office Action dated Mar. 25, 2008.

* cited by examiner

LOADING AND DELIVERY OF SELF-EXPANDING STENTS

PRIORITY

This application is a division of U.S. patent application Ser. No. 10/552,886, now U.S. Pat. No. 8,287,582, which is a U.S. national stage application under 35 U.S.C. §371 of International Application No. PCT/EP2004/004486, filed Apr. 24, 2004, claiming priority to United Kingdom Application No. GB 0309616.1, filed Apr. 28, 2003, each of which is incorporated by reference into this application as if fully set forth herein.

BACKGROUND OF THE INVENTION

This invention relates in one aspect to a method of loading a self-expanding stent into a delivery sheath, in which the stent in a radially confined delivery configuration is advanced axially into the sheath for delivery to a stenting site in which the sheath is withdrawn to release the stent for radial expansion. In another aspect, the invention relates to a self-expanding stent within a percutaneous transluminal delivery catheter that includes a sheath that withdraws proximally to release the stent at a stenting site, and a pusher within the sheath that retains the stent at the site during withdrawal of the sheath.

EP-A-788 332 discloses a self-expanding braided metallic stent tube and a delivery system that includes a soft annulus within the stent lumen that deforms and mechanically engages with the mesh of the stent for restraining the stent from axial movement relative to the inner catheter of the delivery system, during axial movement of a sleeve surrounding the stent. The disclosure of EP-A-596 145 is similar.

EP-A-836 447 discloses a system for delivering a self-expanding stent, in which a stopper ring on an inner catheter abuts the proximal end of the stent tube during proximal withdrawal of a sheath which surrounds the stent.

The number of materials that are biologically compatible, and available for making stents, are comparatively few. One preferred material is stainless steel. One can make stainless steel stents that are plastically deformed when they are expanded radially at the stenting site. One convenient way to expand such stents is by a balloon at the distal end of a balloon catheter. Otherwise, one can design a stainless steel stent to expand elastically when released at a stenting site. Typically, this is achieved by proximal withdrawal of a sheath on the distal end of the delivery catheter, that withdraws proximally to release the stent progressively, starting at its distal end.

Another suitable material is the nickel titanium shape memory alloy known under the trade mark NITINOL. Such stents are typically loaded into a delivery system at a low temperature when the crystal structure of the material is martensitic, and with a memory of a radially expanded shape, characteristic of a higher temperature austenitic crystalline structure. Remarkably, the nickel titanium material is biologically compatible and the martensite/austenite transformation occurs between room temperature and body temperature.

This invention is particularly applicable to self-expanding stents, irrespective of the mechanism of resilient radial expansion at the stenting site. However, the present Applicant has particular experience with nickel titanium shape memory alloy stents and the particular embodiments described below are based on such materials.

The tubular envelope of a stent usually has apertures through its wall thickness to permit radial expansion. Thus, an uncovered or "bare" stent has a tube wall that is normally liquid-permeable. However, there are many occasions when a stent with a liquid-impermeable wall that is not apertured would be desirable. To meet these needs, a family of "covered" stents have been developed. Applicant has particular experience with stent tubes provided with a covering of expanded polytetrafluoroethylene (ePTFE). Typically, the stent tube is covered by luminal and abluminal covering layers of ePTFE, which are bonded to each other through the apertures in the stent tube wall.

During manufacture of stents and delivery systems, attention must be paid to sterility. Specifically, one needs procedures for loading a covered stent into a catheter delivery system that will allow sterile conditions to be maintained, or at least thereafter achieved.

Typically, to introduce a covered self-expanding stent into a catheter delivery system, a tool needs to be provided that compresses the covered stent radially inwardly, down to a diameter which is smaller than the available diameter of the lumen of the delivery system that is to receive the compressed covered stent. Clearly, any structure within the lumen of the stent that resists further inward compression is better avoided, when the objective is to compress the stent radially inwardly as much as the system will tolerate, so as to keep the outside diameter of the delivery system at its distal tip as small as possible.

However, the stent has to be maintained at the stenting site during proximal withdrawal of the surrounding sheath, for progressive release of the stent at the stenting site. If there is no structure within the lumen of the stent, then the entire stress imposed on the stent, to prevent it moving proximally with the proximally withdrawing surrounding sheath, has to be carried on the proximal end annulus of the compressed stent. Often this is not really a problem, especially when the stent is short and not particularly highly compressed radially inwardly, and especially when friction between the compressed stent and the surrounding sheath can be brought to a particularly low value.

Nevertheless, it is important for management of fatigue resistance to avoid imposing on any point of the stent tube a level of stress that is higher than the designed maximum. A stent tube made of metal is susceptible to fatigue failure, if only because it is subject to cyclic stress at the frequency of the heartbeat of the body in which it is installed. For this reason, regulatory authorities require stringent fatigue performance standards which impose on manufacturers of stents and delivery systems an onerous burden to avoid any unforeseen stresses on the stent tube.

The state of the art contains numerous suggestions to use an element within the lumen of the stent to restrain the stent from proximal withdrawal when the surrounding sleeve is withdrawn proximally. However, these systems are of interest only for bare stents, because they rely upon mechanical interaction between surfaces on the stent pusher within the stent lumen, and boundary surfaces of apertures within the wall thickness of the stent tube.

BRIEF SUMMARY OF THE INVENTION

It is an object of the present invention to load self-expanding covered stents into catheter delivery systems which offers better management of stress within the stent tube, facilitates quality control and maintenance of sterile conditions, and is applicable to a range of stent tube designs.

According to one aspect of the present invention, there is provided a method of loading a self-expanding stent into a delivery sheath, as defined in claim 1 below.

By distributing over the full length of the stent tube lumen the forces which necessarily have to be imposed on the stent in order to:
1. load it into a delivery sheath; and/or
2. restrain it from proximal movement during proximal withdrawal of the delivery sheath during placement of the stent at the stenting site one can manage the distribution of stress within the stent tube so that it is distributed more or less homogeneously, rather than concentrated at one end of the stent tube.

By using the covering of the stent as a link in the chain of stress distribution from the pusher to the sheath, one can further avoid any point at all within the metal stent tube which is subject to stress at a level higher than a prescribed design maximum. By their nature, stent coverings are more flexible than the stent tube itself, so have the capability to distribute stress from a point on a metallic stent pusher to an area, or volume, of the material of the stent tube.

Furthermore, the flexibility of the stent covering is sufficient to accommodate the protrusions of the pusher, irrespective where they lie in relation to the apertures of the stent lumen. With the present invention, there is no need to align in any way the protrusions of the stent pusher with the apertures of the stent lumen. Thus, a further technical effect of the present invention is valuable simplicity and speed of operation in loading a range of different covered stent products into their corresponding delivery systems.

Yet a further advantage of the present invention is that the stent pusher needs no undercut or rebated surfaces to achieve its effect, and the pusher has an outside diameter which is smaller than the inside or luminal diameter of the stent tube. These factors give greater reassurance that, when the stent has been placed, and the pusher has to be withdrawn from the stent lumen, there will be no inadvertent or unintended snagging of surfaces of the pusher on surfaces of the covered stent, or indeed of any bodily tissue that might impinge on the surfaces of the stent pusher after it has been withdrawn proximally out of the stent lumen.

Of particular interest in the present invention is a stent pusher with protrusions arranged helically. Such protrusions will achieve the desired pushing effect when the pusher is subject to axial stress. However, arranging the protrusions helically would allow the pusher to be withdrawn from the stent lumen, even while the stent is within the sheath of the delivery system, simply by "unscrewing" the shaft of the pusher until the helical protrusions emerge, by continued rotation of the pusher relative to the stent, out of the lumen of the stent. In this way, one can employ the stent pusher of the present invention as part of a system for loading a covered stent into a sheath, but then remove the pusher, and pass the sheath stent assembly onwards for incorporation into a delivery system which will use an entirely different stent pusher.

BRIEF DESCRIPTION OF THE DRAWINGS

For a better understanding of the present invention, and to show more clearly how the same may be carried into effect, reference will now be made to the accompanying drawings, in which.

DETAILED DESCRIPTION OF THE PREFERRED EMBODIMENTS

Figure 3:
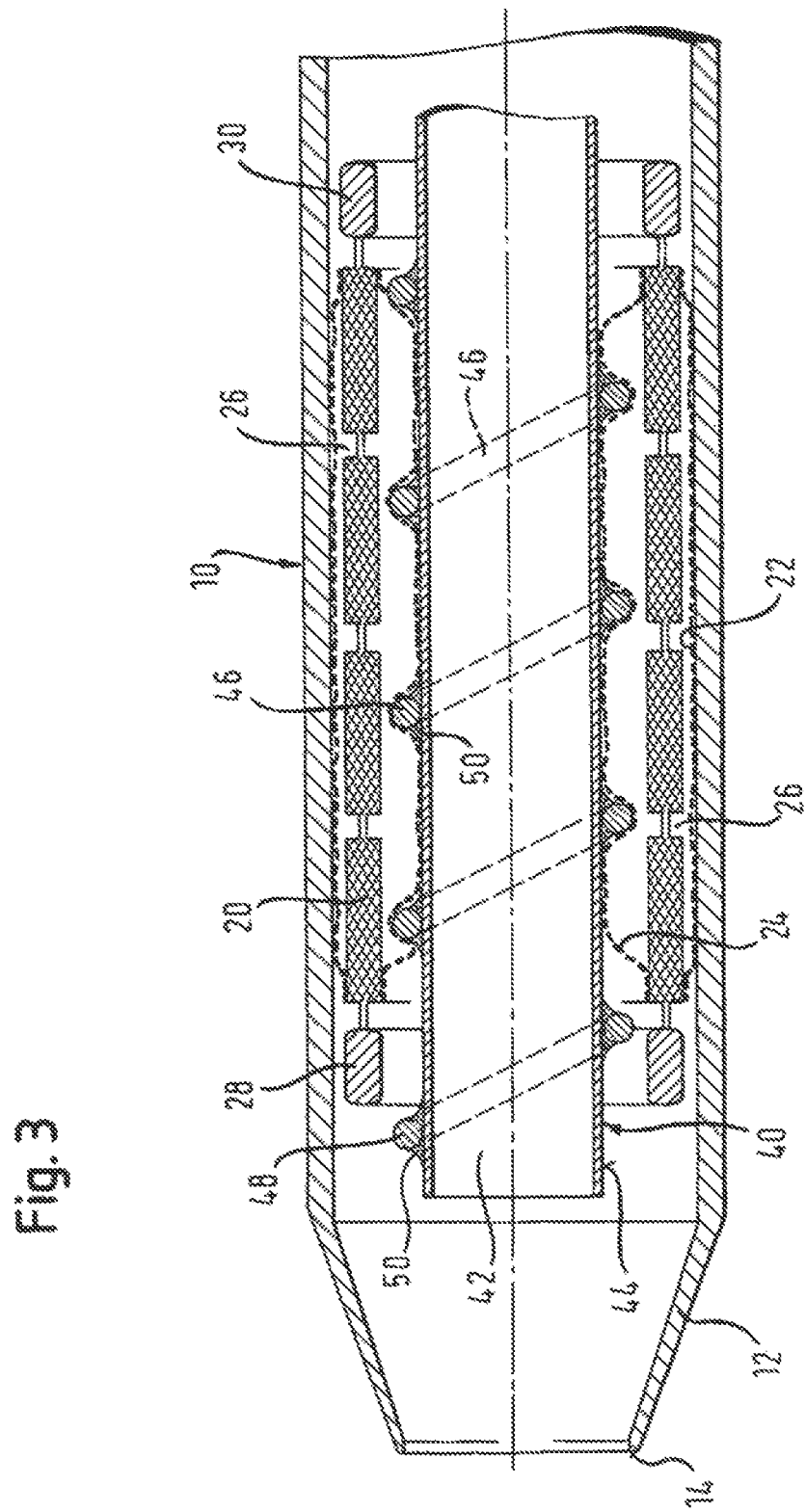
FIG. 3 is an axial diametral section through the distal tip of a stent delivery system which embodies the present invention.

FIG. 3 shows only the distal tip of the delivery system, but the remainder of the system is not part of the contribution which the present invention makes to the art and, in any event, is familiar to those skilled in this art. The basic components of a conventional delivery system for a self-expanding stent are an inner catheter and an outer sheath, the purpose of the outer sheath being to confine the self-expanding stent radially, to the small radius delivery configuration, until its release at the site of stenting. The purpose of the inner catheter is to restrain the stent from proximal movement with the sheath, while the sheath is being withdrawn proximally.

Looking at FIG. 3 of the drawings, the outer sheath 10 of the delivery system has an integral tapered tip 12 which narrows down to an end ring 14 of a diameter appropriate to receive a guidewire (not shown). Confined within the sheath is a covered stent of which the structural foundation is a stent body 20 which is an apertured tube of nickel titanium shape memory alloy. The stent is covered by an outer layer 22 of ePTFE on the abluminal surface of the stent body, and a covering layer 24 of ePTFE on the luminal inner surface of the stent body 20, with the inner and outer layers 24 and 22 being fused together where they can be pressed together within the apertures 26 of the stent body.

Between the luminal and abluminal surfaces of the stent body 20 is a wall thickness of the metallic stent material annulus. This annulus lies between the luminal and abluminal major surfaces of the stent body and, in the specification, we use the terminology "envelope" to indicate the generalised surfaces of the luminal and abluminal major wall surfaces of the stent body. Thus, the outer layer 22 lies outside the abluminal envelope stent body 20, except where it protrudes into the apertures 26 for fusing with the inner layer and, likewise, the inner layer 24 lies radially within the luminal envelope of the stent body 20 except where it protrudes radially outwardly into the stent body apertures 26.

The stent body carries a ring of tantalum radiopaque markers 28 at its distal end and a second ring of radiopaque tantalum markers 30 at its proximal end. It will be appreciated that the presence of these markers may further militate against pushing structures that bear against the end surface of the stent to be deployed.

The inner catheter 40 defines a guidewire lumen 42. Conveniently, the inner catheter 40 is based on a stainless steel hypo tube. This of course endows the entire delivery system with substantial pushability, but the hypo tube can also be made remarkably flexible for the desired trackability of the system through particularly tortuous bodily lumens. In any event, if stainless steel is not flexible enough for the distal zone of the delivery system, then it would be feasible to build the inner catheter 40 from other more flexible materials such as particular polymers.

The stent delivery system can be arranged as an over the wire system with a full length guidewire lumen, or a rapid exchange system with a guidewire lumen only in a distal zone of the system. The outer sheath 10 can be withdrawn by a full length outer catheter or a pull wire within a shaft lumen. For an example of delivery systems of the present Applicant, see WO 03/003944 and WO 2004/062458.

The inner catheter has an abluminal surface 44 which carries on it a wire 46 arranged as a helix so as to provide a plurality of protrusions (at least when seen in section as in the drawing) on the abluminal surface 44. In the illustrated embodiment, the wire is of stainless steel, fixed to the stainless steel tube 40 by deposits 50 of a bonding material which could be a weld bead or a suitable adhesive.

In any event, as can be seen on the drawing, when the stent body is radially inwardly compressed down onto the inner catheter 40, the inner ePTFE layer 24 deforms to accommodate the protrusions 48, but the protrusions 48 do not reach radially outwardly as far as the luminal envelope of the stent body 20.

In use, when the illustrated distal tip zone has been brought to the site of stenting, the outer catheter 12 is carefully and progressively withdrawn proximally so that the tip stretches and slides over the outer ePTFE layer 22 of the stent, progressively releasing the stent, starting at its distal end near the markers 28.

As the stent progressively expands, the inner ePTFE layer 24 moves radially outwardly away from the protrusions 48 until, with complete withdrawal of the tip 12 proximally beyond the proximal ring of radiopaque markers 30, the stent is fully released. It will be appreciated that there is then a substantial annular gap between the lumen of the expanded stent and the envelope containing the protrusions 48, enabling the inner catheter 40 also to be withdrawn proximally from the lumen of the stent without any snagging of the inner catheter 40 on any part of the stent.

It will be appreciated that, for loading a stent into a sheath, an analogous sequence of steps may be performed, with radially inward compression of the stent body down onto the protrusions 48 of a loading tool which has a shape in section analogous to that of the inner catheter 40. Once the stent has been so compressed, a suitable sheath can be offered up to one end of the compressed stent tube, and then the stent can be urged axially into the sheath by imposing an axial force on the line of protrusions 48 through the tube 40 on which they amounted, so that this force is transferred from the protrusions 48 to the inner layer 24 and thence to the stent body 20 and the outer layer 22, so that the entire covered stent device is urged by the protrusions 48 into the receiving sheath.

A particular advantage of the helical structure of protrusions 48 as shown in the drawing is that the pusher within the stent lumen can be removed trouble-free from the lumen of the stent even when it is in a compressed configuration within a sheath as shown in the drawing, simply by "unscrewing" the pusher from within the stent lumen.

Figure 1:
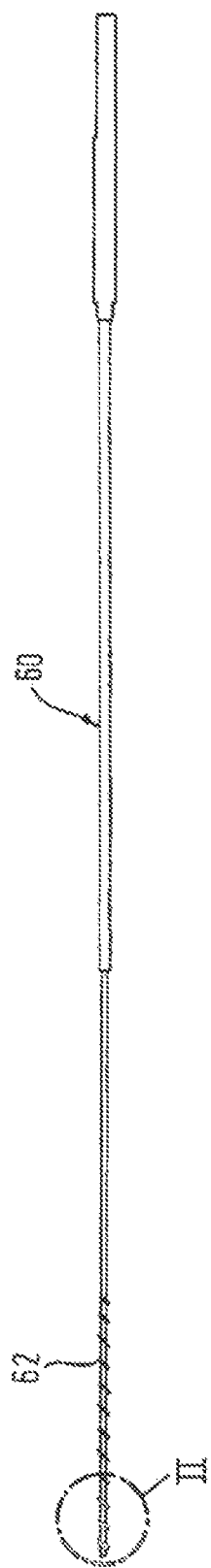
FIG. 1 is a side view of a tool for loading a covered self-expanding stent into a sheath.
Figure 2:
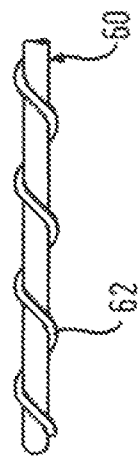
FIG. 2 is an enlarged view of the distal end (II) of the tool of FIG. 1.

Drawing FIGS. 1 and 2 show a suitable loading tool 60, long enough to push the covered stent along the full length of the outer catheter 10, after being compressed and introduced and advanced into the proximal end of the outer catheter. The tool 60 features at its distal end a radially-outwardly protruding wire spiral 62 with a configuration corresponding to that of the protrusions 48 and the inner catheter 40 (although non-corresponding configurations are also feasible). The covered stent is compressed around the protrusions 62 before the tool 60 is used to urge the covered stent by means of the protrusions 62, from the proximal to the distal end of the outer catheter.

The illustrated embodiment shows a system in which the tapered distal tip of the stent delivery system is carried on the distal end of the outer catheter. Those skilled in the art are well-aware that many proposed delivery systems feature a tapered tip on the inner catheter instead. The present invention is just as useful in such systems as it is in systems, as illustrated, with the tapered tip on the outer catheter.

The stent on which the present device operates can be an covered self-expanding stent. The stent which is the basis of the illustrated embodiment is the one that is the preferred embodiment of WO 2002/015820 which is cut from a nickel-titanium tube. However, the invention is equally applicable to other stent design philosophies, such as stents fabricated from wire (one example is the Gianturco "Z" stent made from zig zag wire rings) or other metals, such as stainless steel. The invention is particular useful for covered stents in which only the cover connects adjacent ones of a plurality of stenting rings, because the engagement of the pusher over the full length of the stent should avoid any tendency for the stent covering to "concertina" between the stenting rings when pushed only from its trailing (usually proximal) end.

Those skilled in the art will be able to recognize from this disclosure many other ways to realise the present invention besides that described with reference to the drawings.

What is claimed is:

1. A method of deploying a stent, comprising:
   providing a delivery system with the stent loaded in a reduced diameter configuration between an inner catheter and an outer sheath, the stent including a covering positioned on a luminal wall surface thereof, the inner catheter including a radially outwardly extending protrusion that extends into the covering but does not intersect a plane along the stent luminal wall surface;
   advancing the delivery system to a stenting site; and
   withdrawing the outer sheath to deploy the stent at the stenting site.

2. The method according to claim 1, wherein the withdrawing includes a tip of the outer sheath stretching and sliding over an abluminal wall surface of the stent.

3. The method according to claim 1, wherein the withdrawing includes a tip of the outer sheath stretching and sliding over an outer covering positioned on an abluminal wall surface of the stent.

4. The method according to claim 1, wherein the withdrawing includes withdrawing the outer sheath by moving a proximal end of the outer sheath in a proximal direction.

5. The method according to claim 1, wherein the withdrawing includes using a pull wire within a shaft lumen to proximally move the outer sheath.

6. The method according to claim 1, wherein the outer catheter is a full length outer catheter such that the withdrawing includes pulling on a proximal end of the outer catheter at a proximal end of the delivery system.

7. The method according to claim 1, further comprising withdrawing the inner catheter from the lumen of the stent graft following expansion thereof to an expanded diameter.

8. The method according to claim 1, wherein the withdrawing further comprises longitudinally retaining the stent at the stenting site through an interaction between the protrusion of the inner catheter and the covering of the stent.

9. The method according to claim 1, wherein the withdrawing further comprises moving the covering radially away from the protrusions creating an annular gap between the covering and the protrusion when the outer catheter is completely withdrawn from the stent.

10. The method according to claim 1, wherein the withdrawing further comprises distributing forces imposed during withdrawal over a substantial length of the stent through a plurality of protrusions on the inner catheter spaced along the substantial length of the stent.

11. A method of deploying a stent, comprising:
    providing a delivery system with the stent loaded in a reduced diameter configuration between an inner catheter and an outer sheath, the stent being a covered stent having a matrix with surfaces defining luminal and abluminal envelopes spaced apart by a stent wall thickness, a covering material bonded to the matrix lying radially inside the luminal envelope, the inner catheter including a radially outwardly extending protrusion that extends into the covering but does not reach radially outwardly as far as the luminal envelope;

advancing the delivery system to a stenting site; and withdrawing the outer sheath to deploy the stent at the stenting site.

12. The method according to claim 11, wherein the withdrawing includes a tip of the outer sheath stretching and sliding over the abluminal envelope of the stent.

13. The method according to claim 11, wherein the withdrawing includes a tip of the outer sheath stretching and sliding over an outer covering positioned on an abluminal wall surface of the stent.

14. The method according to claim 11, wherein the withdrawing includes withdrawing the outer sheath by moving a proximal end of the outer sheath in a proximal direction.

15. The method according to claim 11, wherein the withdrawing includes using a pull wire within a shaft lumen to proximally move the outer sheath.

16. The method according to claim 11, wherein the outer catheter is a full length outer catheter such that the withdrawing includes pulling on a proximal end of the outer catheter at a proximal end of the delivery system.

17. The method according to claim 11, further comprising withdrawing the inner catheter from the lumen of the stent graft following expansion thereof to an expanded diameter.

18. The method according to claim 11, wherein the withdrawing further comprises longitudinally retaining the stent at the stenting site through an interaction between the protrusion of the inner catheter and the covering of the stent.

19. The method according to claim 11, wherein the withdrawing further comprises moving the covering radially away from the protrusions creating an annular gap between the covering and the protrusion when the outer catheter is completely withdrawn from the stent.

20. The method according to claim 11, wherein the withdrawing step further comprises distributing forces imposed during withdrawal over a substantial length of the stent through a plurality of protrusions on the inner catheter spaced along the substantial length of the stent.

\* \* \* \* \*